US006706395B2

(12) United States Patent
Harrison et al.

(10) Patent No.: US 6,706,395 B2
(45) Date of Patent: Mar. 16, 2004

(54) RAPIDLY-DISSOLVING HALOGENATED HYDANTOIN POWDERS HAVING IMPROVED FLOW, REDUCED DUST, IMPROVED WETABILITY, AND INCREASED BULK DENSITIES

(75) Inventors: Alan D. Harrison, Douglasville, GA (US); J. Patrick Sisk, Marietta, GA (US)

(73) Assignee: Biolab Services, Inc., Wilmington, DE (US)

(*) Notice: Subject to any disclaimer, the term of this patent is extended or adjusted under 35 U.S.C. 154(b) by 0 days.

(21) Appl. No.: 10/110,268

(22) PCT Filed: Mar. 13, 2001

(86) PCT No.: PCT/US01/07977
§ 371 (c)(1),
(2), (4) Date: Nov. 19, 2002

(87) PCT Pub. No.: WO01/68535
PCT Pub. Date: Sep. 20, 2001

(65) Prior Publication Data
US 2003/0211323 A1 Nov. 13, 2003

Related U.S. Application Data
(60) Provisional application No. 60/188,823, filed on Mar. 13, 2000.

(51) Int. Cl.$^7$ .............................. B32B 5/16; C02F 1/76; C07D 233/00
(52) U.S. Cl. ...................... 428/402; 210/754; 210/755; 548/311
(58) Field of Search .......................... 428/402; 548/311; 210/754, 755

(56) References Cited

U.S. PATENT DOCUMENTS

| | | | | |
|---|---|---|---|---|
| 3,328,294 A | * | 6/1967 | Self et al. ................... 210/744 |
| 3,412,021 A | * | 11/1968 | Patterson .................... 210/667 |
| 4,427,692 A | * | 1/1984 | Girard ......................... 514/390 |
| 4,621,096 A | * | 11/1986 | Cole ............................ 514/389 |
| 4,654,424 A | * | 3/1987 | Girard et al. ............ 548/320.5 |
| 5,565,109 A | * | 10/1996 | Sweeny ...................... 210/755 |
| 6,429,181 B2 | * | 8/2002 | Sweeny et al. ............. 510/382 |
| 6,495,698 B1 | * | 12/2002 | Howarth .................. 548/320.5 |
| 6,508,954 B1 | * | 1/2003 | Elnagar et al. ............. 252/180 |

* cited by examiner

Primary Examiner—H. Thi Le
(74) Attorney, Agent, or Firm—Woodard, Emhardt, Moriarty, McNett & Henry LLP (57) ABSTRACT

A powdered halogenated hydantoin product having the following size distribution: (a) 70–100% halogenated hydantoin particles sized between 80 mesh and 200 mesh; (b) 0–20% particles sized larger than 80 mesh; and (c) 0–10% particles sized smaller than 200 mesh. The powdered product has superior dissolution and flow characteristics, while avoiding dusting where the product is used. Bromochlorodimethylhydantoin is the preferred halogenated hydantoin.

8 Claims, 5 Drawing Sheets

RAPIDLY-DISSOLVING HALOGENATED HYDANTOIN POWDERS HAVING IMPROVED FLOW, REDUCED DUST, IMPROVED WETABILITY, AND INCREASED BULK DENSITIES

This application is a 371 of PCT/US01/07977 Mar. 13, 2001 which claims benefit of 60/188,823 Mar. 13, 2000.

FIELD OF THE INVENTION

The present invention relates generally to halogenated hydantoins, and more particularly to rapidly dissolving halogenated hydantoin powders (particularly BCDMH powder) with improved flow, decreased dust, improved wetability, and increased density.

BACKGROUND OF THE INVENTION

One of the most pervasive problems in the paper making industry is the growth of biological organisms that interfere with the manufacturing process or negatively impact the quality of the finished paper. These organisms typically form into slimes on the machines, which can then become incorporated into the paper. Slimes in paper can affect paper quality, and accordingly may affect the profitability of the mill. Slimes in the paper can also lead to "slime tears" during the papermaking process, which may require the machine to be shut down and restarted. Shut downs also can have a large effect on the profitability of the mill, due to the high capital cost associated with papermaking. Additionally, slimes in the paper may also cause unwanted tastes and odors, again affecting paper quality and mill profitability.

Historically, paper mills have used chemical treatments in conjunction with periodic shut downs to control biological fouling. Most commonly, chlorine or non-oxidizing biocides have been used in those treatments. Unfortunately though, chlorine presents handling and discharge problems, while non-oxidizing biocides often have limited efficacy and can be very expensive.

The halogenated hydantoin bromochlorodimethylhydantoin ("BCDMH") has been used successfully in the cooling water and process industries because of its generally good handling and discharge characteristics, as well as its superior efficacy. Some problems remain, however, that limit the utility of BCDMH in paper mills. For example, the trend in the paper industry is to "close" mills, which means more water is recycled, less fresh water is used, and less wastewater is discharged. This means that less fresh water is available in the mill for various uses, and the mill is more sensitive to the addition of fresh water because of water and chemistry balances. Because the most common forms of BCDMH—tablets and granules—require large amounts of relatively clean water to dissolve, their use is limited in the paper manufacturing process.

As an alternative to tablets and granules, BCDMH powder has been available for several years. It provides the advantage of a "quick dissolving" product in markets where this is critical because of the limited availability of fresh water. However, several other issues remain, particularly regarding flowability, dusting, wetability, and bulk density. From the flowability standpoint, powdered BCDMH frequently exhibits variable rates of flow, leading to inconsistent amounts of feed. From the dusting standpoint, the product has been very dusty, making it inconvenient to handle and sometimes requiring the use of respirators or other air purification systems. From the wetability standpoint, the product, because of a portion of its small particle size, expresses difficulty in wetting, and tends to float on the surface in the mixing tank, rather than forming a suspension. From the density standpoint, the product is fluffy and light in appearance and weight, which requires larger and more costly packaging.

A need therefore exists for new powdered halogenated hydantoin products that meets the requirements for improved flow, reduced dust, improved wetability, and increased density. The present invention addresses that need.

SUMMARY OF THE INVENTION

Briefly describing one aspect of the present invention, powdered halogenated hydantoin products such as BCDMH are prepared to provide the following particle size distribution: (a) 70–100% halogenated hydantoin particles sized between 80 mesh and 200 mesh; (b) 0–20% particles sized larger than 80 mesh; and (c) 0–10% particles sized smaller than 200 mesh. These powdered products have superior dissolution and flow characteristics, with reduced dusting, improved wetability, and increased density when compared to prior art products.

In another aspect of the present invention the powdered halogenated hydantoin products are prepared to provide the following particle size distribution: (a) 90–100% halogenated hydantoin particles sized between 60 mesh and 200 mesh; (b) 0–5% particles sized larger than 60 mesh; and (c) 0–5% particles sized smaller than 200 mesh.

One object of the present invention is to provide BCDMH compositions having improved flowability, reduced dusting, improved wetability, and increased density.

Other objects and advantages will be apparent from the following description of the preferred embodiments.

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the preferred embodiments, and such further applications of the principles of the invention as described herein being contemplated as would normally occur to one skilled in the art to which the invention pertains.

As briefly described above, one aspect of the present invention provides powdered halogenated hydantoin compositions having improved flowability, reduced dusting, improved wetability, and increased density, while maintaining satisfactory dissolution rates. These powdered products are particularly useful for treating water in paper mills and other industrial applications, including, but not limited to, cooling water, breweries, food applications, and other process waters.

The inventive halogenated hydantoin powders have a specific particle size distribution. In general, the particles are small enough to provide rapid dissolution in water or other aqueous solutions, yet large enough to provide reduced dustiness and consistent, reliable flow. It has been found that the following particle size distribution provides those characteristics:

(a) 70–100% particles sized between 80 mesh and 200 mesh;

(b) 0–20% particles sized larger than 80 mesh; and (c) 0–10% particles sized smaller than 200 mesh.

More preferably, the halogenated hydantoin powders of the present invention have the following particle size distribution:

(a) 90–100% particles sized between 60 mesh and 200 mesh;

(b) 0–5% particles sized larger than 60 mesh; and (c) 0–5% particles sized smaller than 200 mesh.

As indicated above, the inventive powders comprise any of the halogenated hydantoins, including any or all of the mono- or di-halogenated hydantoins. Most preferably, the powders comprise a substantial amount of bromochlorodimethylhydantoin, with powders comprising 20–70% BCDMH being most preferred. The remainder of the halogenated hydantoin powder preferably includes other mono- or di-halogenated dialkylhydantoins, such as chlorobromodimethylhydantoin, dibromodimethylhydantoin, dichlorodimethylhydantoin, dichloromethylethylhydantoin, etc.

The halogenated hydantoins used to make the inventive powders are made by conventional methods, as is known to the art. A slurry is typically produced, and is then dried (e.g., by centrifuging and/or flash drying). The small (typically five- to ten-micron sized) particles thus produced are compacted/agglomerated to increase their particle size, using conventional compaction or agglomeration techniques.

The material is then screened to separate out the particles that are too large or too small. The larger particles can then be reduced in size using a ball mill, hammer mill, air mill, etc. Smaller particles can be returned to the compaction/agglomeration step.

It is to be appreciated that standard production processes make a powder that consists essentially of the desired halogenated hydantoin, but that up to about 15% salt and other minor by-products are normally also included in the mixture. For the purposes of this disclosure, the halogenated hydantoin powders are described with respect to their halogenated hydantoin component only, it being recognized that other production by-products are necessarily present in relatively minor amounts. Accordingly, a powder that consists essentially of halogenated hydantoin particles is a powder that consists essentially of halogenated hydantoin and the relatively minor amounts of salt and other by-products that would naturally occur with standard production processes.

The halogenated hydantoin powders of the present invention provide acceptable flow characteristics for use in the paper industry, as will be shown by the example(s) below. Under-feed of product is avoided, as is the build up of biological fouling with all its associated problems. Over-feed of product is also avoided, as are high treatment costs and the potential for corrosion of the paper machine.

The halogenated hydantoin powders of the present invention also provide acceptable "dusting" characteristics, as will be shown below. While dusting is a complex phenomenon that is not fully understood, it is known that small particle size materials tend to be more dusty, and the addition of "work" (e.g, from granule compactors in the production process) can also make material dustier. This may be related to electrostatic charge on individual particles. The inventive powders reduce dusting by reducing the amount of smaller particles and increasing the amount of larger particles.

In particular, the inventive powders have a measured dust level of no more than about 0.4% (when measured as described in Example 4 below), with dust levels of less than about 0.2% being more preferred, and dust levels of less than about 0.1% being most preferred.

The halogenated hydantoin powders of the present invention also provide acceptable "wetability" characteristics, as will be shown below. Wetability is an important factor in preparing a suspension (or slurry) of product to be pumped to specific treatment sites. Specialized equipment must be used to feed this product due to the corrosivity and cohesiveness of the product. The product is feed by a screw auger into a mixing tank while adding water at a specific rate. The inventive process will insure that a homogeneous mixture is maintained within the mixing tank and that no material will remain floating on the surface of the tank. An additional problem with low wetability products is the tendency for material to build up in and around the aforementioned slurry tank. This material must be cleaned by hand thus causing potential worker exposure and is also aesthetically objectionable to personnel.

The halogenated hydantoin powders of the present invention also provide acceptable product densities. Since specialized packaging must be employed to transport and store the material, a higher, more consistent product density will reduce overall production costs as will be shown below.

Finally, the halogenated hydantoin powders of the present invention also provide acceptable dissolution characteristics for use in industry. Because the throughput of water in a water system can be as short as several minutes, the halogenated hydantoin material must go into solution rapidly. Because dissolution rate is directly proportional to the surface area of the particles, rapid dissolution is best achieved with small particles. Surprisingly it has been found that even though the inventive powders are made of particles that are large enough to have superior flow, reduced dust, improved wetability, and increased density, they are still small enough to provide rapid dissolution.

In the preferred embodiments the inventive powders dissolve at a rate such that at least 80% of the material is dissolved in ambient temperature water in less than twelve (12) minutes, when measured as described in Example 2. The more preferred embodiments provide dissolution rates of 80% in less than ten (10) minutes, while the most preferred embodiments provide dissolution rates of 90% in less than nine (9) minutes.

In the preferred embodiments the inventive powders dissolve at a rate such that at least 80% of the material is dissolved in 35° C. water in less than ten (10) minutes, when measured as described in Example 3. The more preferred embodiments provide dissolution rates of 80% in less than eight (8) minutes, while the most preferred embodiments provide dissolution rates of 90% in less than six (6) minutes.

The powders of the present invention find particular utility in the paper industry, although other applications (e.g., cooling water treatment, waste water treatment, etc.) may also be developed. In general, the powders are particularly useful when there is a need for a product that is easy to feed (i.e., flows consistently without dusting) and has rapid dissolution, or is required in large quantities.

In all of the anticipated applications, the powders are applied by contacting the water to be treated with a sufficient amount of the powder(s). Feeders, etc., may be used to facilitate delivering the powder to the water. The amount of powder necessary to effect adequate water treatment depends on the nature of the water being treated, and on the requirements for treatment efficacy, as is known to the art.

Reference will now be made to specific examples illustrating the preferred embodiments. It is to be understood that the examples are provided to more completely describe preferred embodiments, and that no limitation to the scope of the invention is intended thereby.

EXAMPLE 1

BCDMH powders having the particle size distribution disclosed herein are made using conventional methods. The powdered product is removed from the reactor, and is dried using centrifuging and flash drying.

The material is then increased in size using a roll compactor. Following compaction, the material is scalped using a 60 or 80 mesh screen to remove all material larger than desired. The material is then passed through a Turbo-Screener, Air Classifier, or other size classification devices to remove fine material using a 200 mesh screen or equivalent separation.

The produced product consists essentially of BCDMH powder, particularly consisting of about 85% or more BCDMH and about 15% or less salt.

EXAMPLE 2

The rapid-dissolution property of the inventive BCDMH powders were confirmed by measuring dissolution rates for the inventive and prior art BCDMH powders using the method described below at a temperature of about 25° C. The general goal for dissolution is to achieve a dissolution rate similar to that of currently available BCDMH powders (e.g., BromiCide® powder from Bio-Lab, Inc.), while a more specific goal is to produce a material, which dissolves at the 90% level in no more than 5–10 minutes.

Method

1. Flush a mixing tank with de-ionized water and fill to a predetermined level.
2. Mix the water in the tank with a mixer set at 850 rpm. Use a tank circulation system capable of turning the tank volume over at least once every 5 minutes.
3. Determine and obtain the amount of sample needed and place into the water tank.
4. Remove a sample of water with a large syringe and filter into a disposable centrifuge tube.
5. This process is performed for each of the timed intervals, as quickly as possible.
6. Transfer the filtered water from the vial to the sample cell. Wash the cell a couple of times with this water before filling it to the 10 ml mark.
7. Clean the outside of the cell and place into the calorimeter. Press zero, then press read. The value 0.00 should be displayed both times.
8. Add one packet of DPD Total Chlorine to the cell, shake for 20 seconds, and then let stand for three minutes before taking a reading.
9. A blank must be run to assure the tank is free of any halogens. This is performed before any sample is added. An acceptable initial value is between 0.00 and 0.03 mg/L $Cl_2$.
10. The water temperature should remain around 23–26° C. Samples should be taken at frequent time intervals to insure that enough data is obtained to make a plot of the amount dissolved vs time.
11. Plot the data and determine the maximum level of halogen obtained. Determine the time required for 90% of the material to go into solution.

Figure 1:
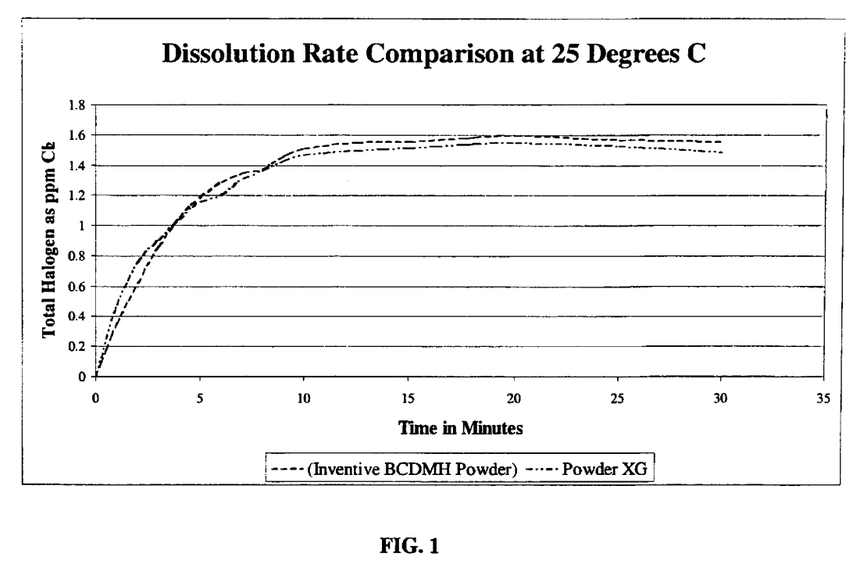
FIG. 1 is a graph showing dissolution rates for the current invention and Powder XG at 25° C.
Figure 2:
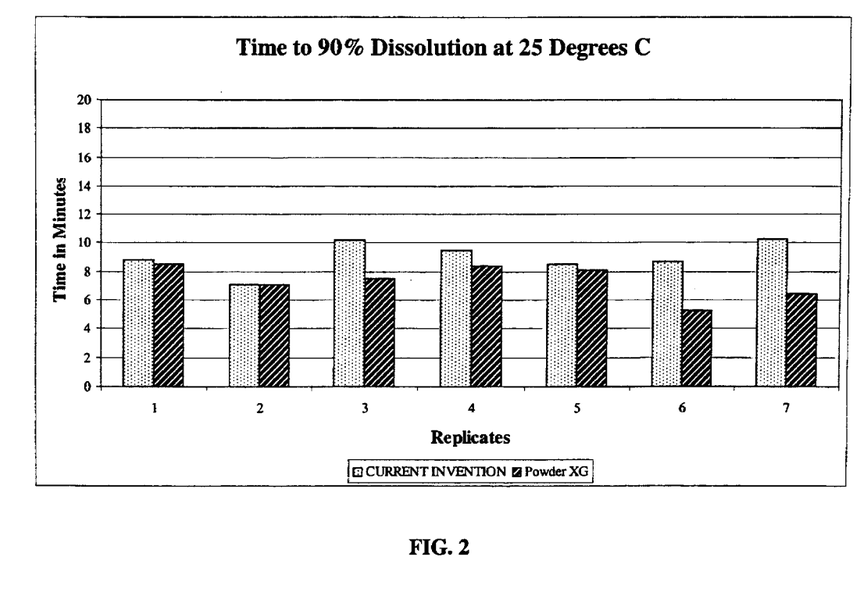
FIG. 2 is a chart showing dissolution times at 90% for the current invention and Powder XG at 25° C.

Calculations: (refer to Table 1 below)
Maximum Values: Current Invention=1.59 ppm
Powder XG=1.55 ppm The dissolution concentration at 90% is around 1.44 ppm for the current invention, and about 1.40 ppm for Bromi-Cide® Powder XG. As can be seen from the graphs shown in FIGS. 1 and 2, and from Table 1 below, both the inventive BCDMH powder and the current Powder XG dissolved to the 90% level in less than 9 minutes. Table 2 below relates calculated dissolution times to the 90% level for samples of the current invention and Powder XG at 25° C.

TABLE 1

Dissolution data for products at 25° C.

| (Minutes) | Halogen in ppm as $Cl_2$ | |
| --- | --- | --- |
| | Current Invention | Powder XG |
| 0.0 | 0.00 | 0.00 |
| 1 | 0.35 | 0.48 |
| 2 | 0.62 | 0.76 |
| 3 | 0.86 | 0.91 |
| 4 | 1.05 | 1.04 |
| 5 | 1.19 | 1.16 |
| 6 | 1.29 | 1.20 |
| 7 | 1.35 | 1.31 |
| 8 | 1.38 | 1.37 |
| 9 | 1.46 | 1.43 |
| 10 | 1.51 | 1.47 |
| 12.5 | 1.55 | 1.50 |
| 15 | 1.56 | 1.52 |
| 17.5 | 1.58 | 1.54 |
| 20 | 1.599 | 1.55 |
| 25 | 1.57 | 1.53 |
| 30 | 1.56 | 1.49 |
| 40 | 1.58 | — |
| 50 | 1.55 | — |
| 60 | 1.57 | — |

TABLE 2

Calculated dissolution times for CURRENT INVENTION and Powder XG samples at 25° C.
Dissolution Times (minutes) for 90% Level

| Current Invention | Powder XG |
| --- | --- |
| 8.8 | 8.5 |
| 7.1 | 7.1 |
| 10.2 | 7.5 |
| 9.5 | 8.4 |
| 8.5 | 8.1 |
| 8.7 | 5.3 |
| 10.3 | 6.4 |

EXAMPLE 3

The rapid-dissolution property of the inventive BCDMH powders were confirmed by measuring dissolution rates for the inventive and prior art BCDMH powders using the method described in Example 2, but at a temperature of about 35° C. The general goal for dissolution is to achieve a dissolution rate similar to that of currently available BCDMH powders (e.g., BromiCide® powder from Bio-Lab, Inc.), while a more specific goal is to produce a material, which dissolves at the 90% level in no more than 5–10 minutes.

Calculations: (refer to Table 3 below)

Maximum Values: Current invention=1.61 ppm

Powder XG=1.50 ppm

Figure 3:
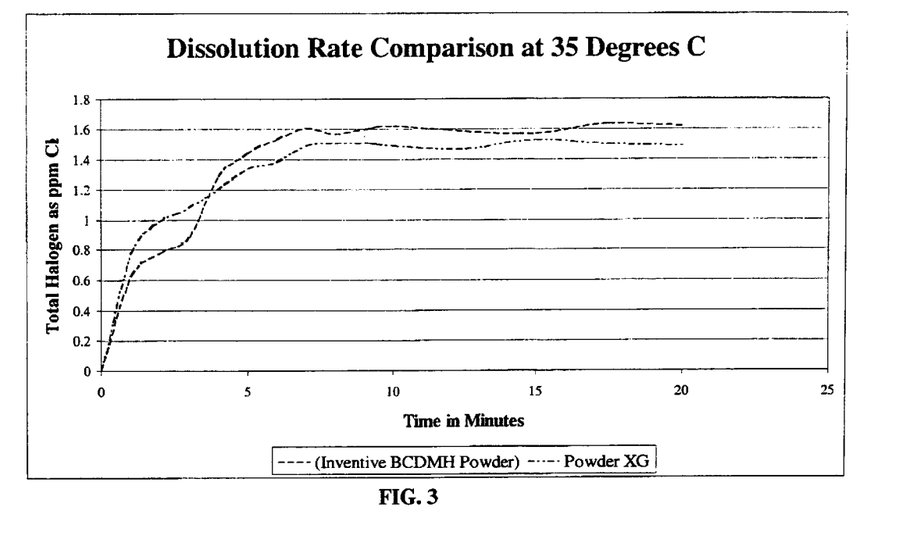
FIG. 3 is a graph showing dissolution rates for the current invention and Powder XG at 35° C.
Figure 4:
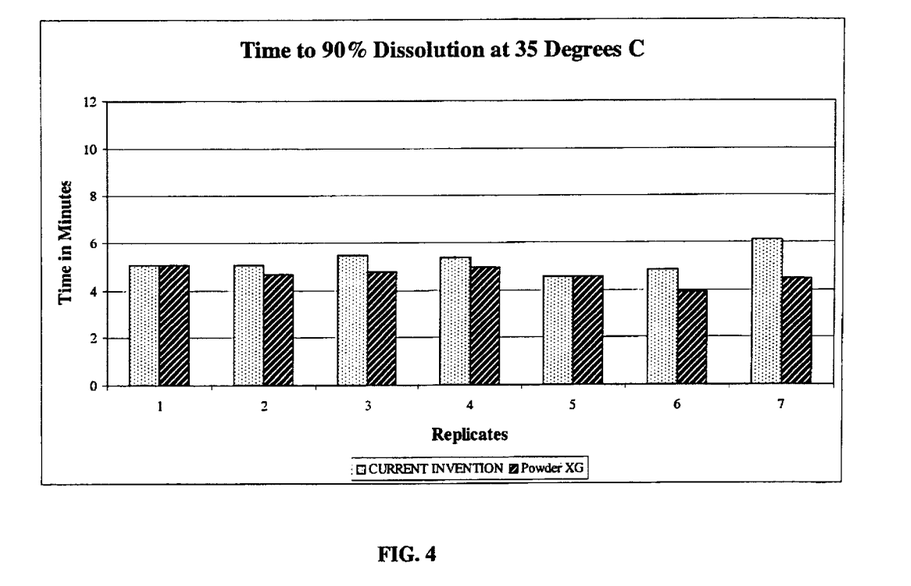
FIG. 4 is a chart showing dissolution times at 90% for the current invention and Powder XG at 35° C.

The dissolution concentration at 90% is around 1.45 ppm for current invention and 1.44 ppm for BromiCide® Powder XG. As can be seen from FIG. 3, FIG. 4, and Table 3 below, both the inventive BCDMH powder and the current Powder XG dissolved to the 90% level in about 5 minutes. Table 4 below relates calculated dissolution times to the 90% level for samples of the current invention and Powder XG at 35° C.

TABLE 3

Dissolution data for products at 35° C.

Halogen in ppm as $Cl_2$

| (Minutes) | CURRENT INVENTION (Inventive BCDMH Powder) | Powder XG |
| --- | --- | --- |
| 0.0 | 0.01 | 0.00 |
| 1 | 0.63 | 0.78 |
| 2 | 0.78 | 0.99 |
| 3 | 0.89 | 1.08 |
| 4 | 1.29 | 1.20 |
| 5 | 1.44 | 1.34 |
| 6 | 1.53 | 1.38 |
| 7 | 1.61 | 1.49 |
| 8 | 1.57 | 1.51 |
| 9 | 1.60 | 1.51 |
| 10 | 1.62 | 1.49 |
| 12.5 | 1.59 | 1.47 |
| 15 | 1.57 | 1.53 |
| 17.5 | 1.64 | 1.50 |
| 20 | 1.62 | 1.49 |
| 25 | 1.58 | — |
| 30 | 1.61 | — |

TABLE 4

Calculated dissolution times for current invention and Powder XG samples at 35° C.
Dissolution Times (minutes) for 90% Level

| CURRENT INVENTION | Powder XG |
| --- | --- |
| 5.1 | 5.1 |
| 5.1 | 4.7 |
| 5.5 | 4.8 |
| 5.4 | 5.0 |
| 4.6 | 4.6 |
| 4.9 | 3.9 |
| 6.1 | 4.5 |

EXAMPLE 4

The "dusting" of the inventive BCDMR powders were tested using a method from the CIPAC Handbook modified below (W. Dobrat and A. Martin, "MT171 Dusting of Granular Products," *CIPAC Handbook, Physico-chemical Methods for Technical and Formulated Pesticides*, Volume F, 1995, 425–429).

Method

1. Clean crucible and place a filter in the bottom. Weigh to the nearest 0.001 gram to determine the tare weight. Be sure all fingerprints and foreign particle are removed from the crucible before weight is obtained.
2. Place the crucible in the opening in the bottom box using the elastic bands to help seal the opening. Place the lid with the long cylinder tube on the box and screw down.
3. Insert the stopper into the opening at the top of the tub.
4. Obtain approximately a five gram sample and place on top of the stopper.
5. Remove the stopper and allow one second to pass before the vacuum is activated and the 60 second timer is started. Make any adjustments necessary to keep the pressure at 0.7 SCFM.
6. When test is complete remove the lid and crucible. Carefully clean any stray particle that may be lying on the inside or around the outside of the crucible with kimwipes®.
7. Weigh the crucible to obtain the gross weight. The percent dust is determined by the subtracting the tare weight from the gross weight and dividing by the sample weight and multiplying by 100 percent.
8. The entire apparatus needs to be cleaned before the next test can be run.

Calculations and Results

% Dust=((Gross weight−Tare weight)/sample weight)*100%

The following data in Table 5 tabulates % Dust values for both Powder XG and the present invention. The inventive powders reduced dusting by more than 90%, and thus satisfied the stated requirements for reduced dusting.

TABLE 5

% Dust Values for current invention and Powder XG.
% Dust Values

| CURRENT INVENTION | Powder XG |
| --- | --- |
| 0.08 | 0.67 |
| 0.07 | 0.86 |
| 0.17 | 0.79 |
| 0.03 | 0.86 |
| 0.05 | 0.82 |
| 0.08 | 0.81 |
| 0.08 | 0.71 |

EXAMPLE 5

The flow characteristics of the inventive BCDMH powders were investigated by testing the powder under the conditions that would be experienced in a paper making plant. The inventive powders had superior flow when compared to prior art powders. Comparisons of flow were made by feeding the material with a typical powder feeder device used in the field at a paper making plant. Measurement ranges were determined for the amount of material dispensed for one (1) revolution of the feeding screw. Table 6 below compares data obtained from the current invention, Powder XG, and Lonza's BCDMH Powder.

TABLE 6

Feed Rate data for various samples.

| Product | Feed Rate (grams/revolution) |
| --- | --- |
| Current Invention | 110–120 |
| Powder XG | 90–100 |
| Lonza Material | 69–75 |

EXAMPLE 6

The density of the inventive BCDMH powders were evaluated by making measurements of bulk density and tap density using the method described below.

Bulk Density Method

1. Determine the tare weight (g) of a 100 ml graduated cylinder.
2. Add BCDMH material to the 100 ml line and determine the gross weight (g) of the cylinder and the sample.
3. Determine the bulk density in grams/L by using the formula:

Bulk Density=(Gross Weight (g)−Tare Weight (g))/(0.100 L)

Tap Density Method

1. Take the sample of material and graduated cylinder from the Bulk Density Test above.
2. Gently tap the bottom of the cylinder on the counter to compact the material.
3. Tap a total of 50 times. Record the final volume of the material in L.
4. Determine the tap density in grams/L by using the formula:

Tap Density=(Gross Weight (g)−Tare Weight (g))/(Final Volume (L))

The data in table 7 below compares the bulk density and tap density from the current invention and Powder XG. The data indicates that the current invention has a much higher bulk density indicating a much more compact material. The data also indicates that the Powder XG may compact some, but will not have near the same tap density as the current invention.

TABLE 7

Bulk density and Tap density measurements for current invention and Powder XG.

| Current Invention | | Powder XG | |
|---|---|---|---|
| Bulk Density (Grams/L) | Tap Density (Grams/L) | Bulk Density (Grams/L) | Tap Density (Grams/L) |
| 879.5 | 993.8 | 660.2 | 835.7 |
| 874.7 | 994.0 | 657.9 | 812.2 |
| 882.0 | 991.0 | 662.1 | 817.4 |

EXAMPLE 7

The wetability of the current invention and powder XG was measured in the laboratory and observed at an on-site application during a recent field trial. The laboratory method is described below.

1. Fill a 1000 ml beaker with 500 ml deionized water.
2. Add 10 grams of sample to the top of the water.
3. Gently mix to simulate mixing tank.
4. Determine the time necessary for the material to settle to the bottom of the beaker.

Table 8 below shows wetability data for the current invention and Powder XG. A specific observation that was made during the test stated that a portion of the Powder XG material agglomerated on the surface into chucks and settled to the bottom of the beaker. These agglomerates were not wetted properly and remanded as agglomerates on the bottom of the beaker throughout the remainder of the test. The time that was recorded was the time that the bulk of the material settled to the bottom of the cylinder. This test shows the superior wetability characteristics of the current invention.

TABLE 8

Wetability Data in minutes for current invention and Powder XG.
Wetability Data for Current Invention and Powder XG (minutes)

| Current Invention | Powder XG |
|---|---|
| 8 minutes | >13 minutes |

Figure 5:
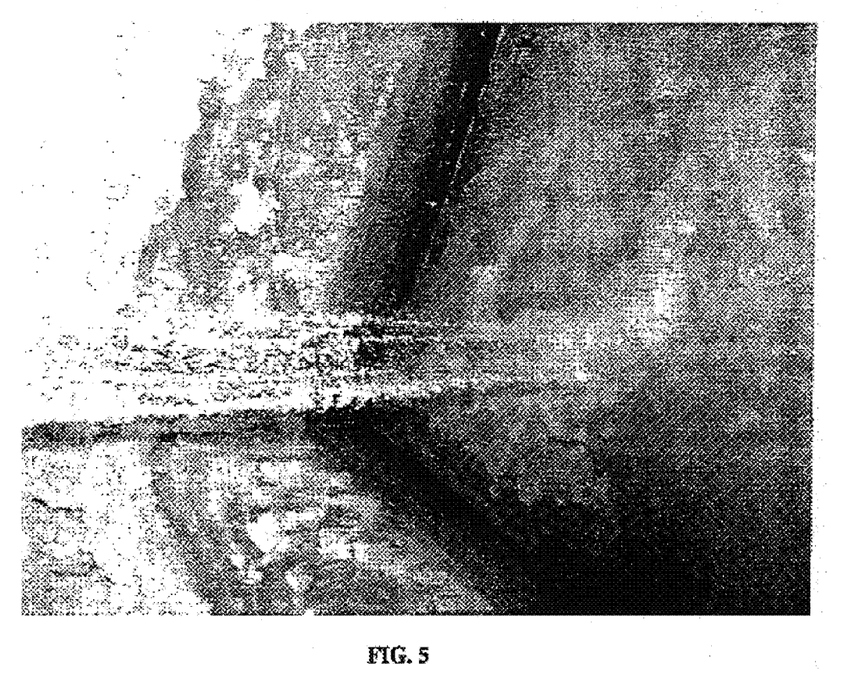
FIG. 5 shows the current invention as it feeds into the mixing chamber.
Figure 6:
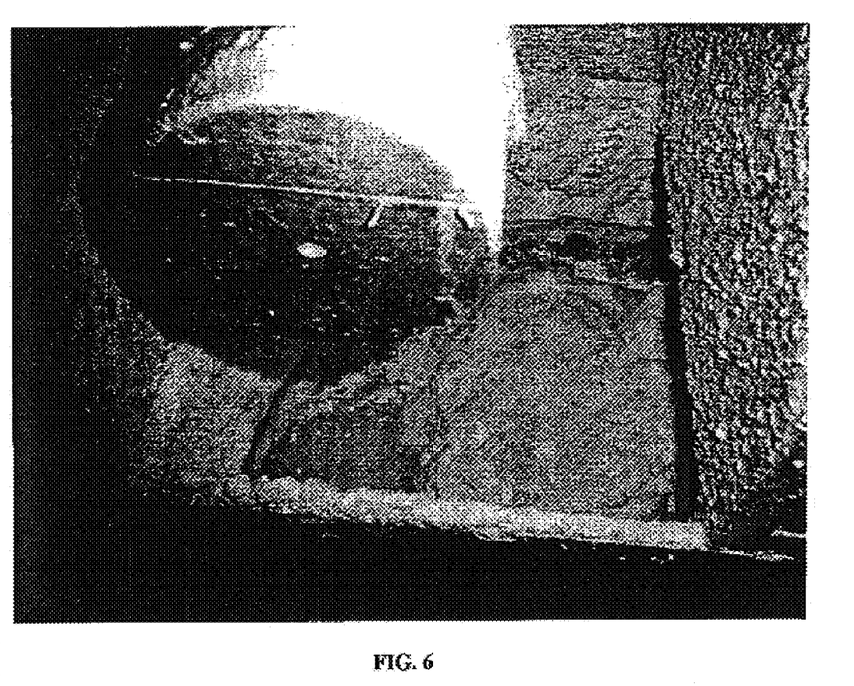
FIG. 6 shows the Powder XG as it feeds into the mixing chamber.
Figure 7:
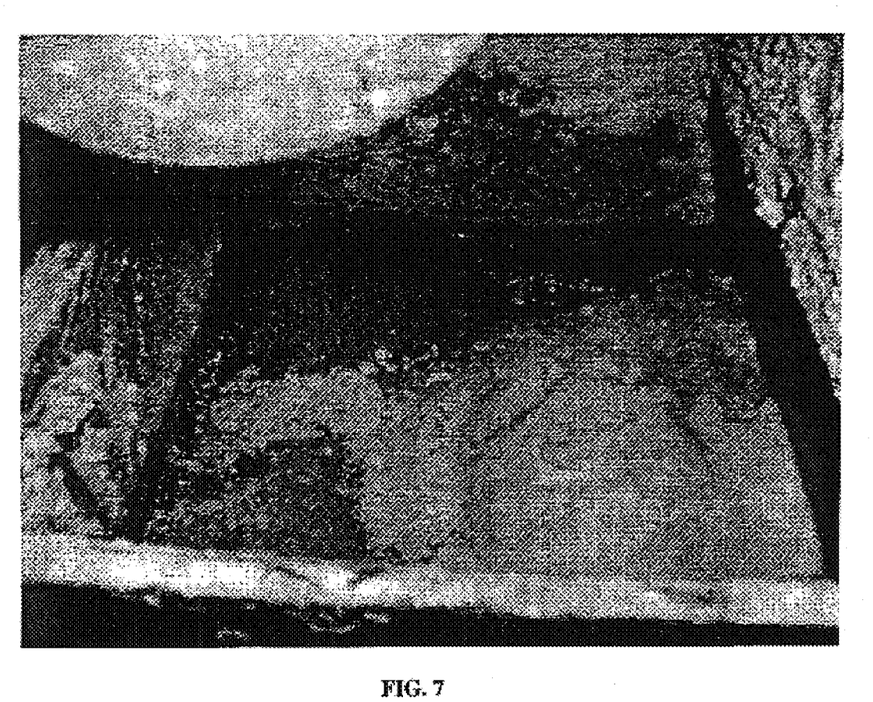
FIG. 7 shows a competitor's product as it is fed into the mixing chamber.

A field application was performed with the current invention to prove product usability. Several pictures were taken of the mixing chamber to show wetting properties and are shown in FIGS. 5, 6, and 7. FIG. 5 shows the current invention as it is added to the mixing chamber. It is apparent that there is little or no material floating on the surface with minimal frothing/foaming. The pictures related in FIGS. 6 and 7 show Powder XG and a competitor's product. In both pictures, there is a considerable amount of frothing and material floating on the surface of the mixing chamber. This floating material is an example of an inconsistent mix due to poor wetting properties.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

We claim:

1. A powdered halogenated hydantoin product consisting essentially of:
   (a) 70–100% halogenated hydantoin particles sized between 80 mesh and 200 mesh;
   (b) 0–20% halogenated hydantoin particles sized larger than 80 mesh; and
   (c) 0–10% halogenated hydantoin particles sized smaller than 200 mesh.

2. The powdered halogenated hydantoin product of claim 1 wherein the powdered halogenated hydantoin product consists essentially of:
   (a) 90–100% halogenated hydantoin particles sized between 60 mesh and 200 mesh;
   (b) 0–5% halogenated hydantoin particles sized larger than 60 mesh; and
   (c) 0–5% halogenated hydantoin particles sized smaller than 200 mesh.

3. The powdered halogenated hydantoin product of claim 2 wherein the powdered halogenated hydantoin is bromochlorodimethylhydantoin.

4. The powdered halogenated hydantoin product of claim 1 wherein the powdered halogenated hydantoin is bromochlorodimethylhydantoin.

5. A method of treating water, said method comprising adding to the water a water treatment composition comprising powdered halogenated hydantoin; wherein said halogenated hydantoin consists essentially of:
   (a) 70–100% halogenated hydantoin particles sized between 80 mesh and 200 mesh;
   (b) 0–20% halogenated hydantoin particles sized larger than 80 mesh; and
   (c) 0–10% halogenated hydantoin particles sized smaller than 200 mesh.

6. The method of claim 5 wherein said powdered halogenated hydantoin product consists essentially of:

(a) 90–100% halogenated hydantoin particles sized between 60 mesh and 200 mesh;
(b) 0–5% halogenated hydantoin particles sized larger than 60 mesh; and
(c) 0–5% halogenated hydantoin particles sized smaller than 200 mesh.

7. The method of claim 6 wherein the powdered halogenated hydantoin is bromochlorodimethylhydantoin.

8. The method of claim 5 wherein the powdered halogenated hydantoin is bromochlorodimethylhydantoin.

* * * * *